United States Patent
Samadani et al.

(10) Patent No.: US 11,937,935 B2
(45) Date of Patent: Mar. 26, 2024

(54) METHODS AND KITS FOR DETECTION OF BLAST BRAIN INJURY, ITS SEVERITY, DISTANCE FROM BLAST EPICENTER, AND CLASSIFICATION RELATIVE TO THE LARGER SPECTRUM OF CONCUSSION

(71) Applicant: HENNEPIN HEALTHCARE SYSTEM, INC., Minneapolis, MN (US)

(72) Inventors: Uzma Samadani, Minneapolis, MN (US); Abdullah Bin Zahid, Minneapolis, MN (US)

(73) Assignee: HENNEPIN HEALTHCARE SYSTEM, INC., Minneapolis, MN (US)

( * ) Notice: Subject to any disclaimer, the term of this patent is extended or adjusted under 35 U.S.C. 154(b) by 877 days.

(21) Appl. No.: 16/966,181

(22) PCT Filed: Jan. 25, 2019

(86) PCT No.: PCT/US2019/015245
§ 371 (c)(1),
(2) Date: Jul. 30, 2020

(87) PCT Pub. No.: WO2019/148003
PCT Pub. Date: Aug. 1, 2019

(65) Prior Publication Data
US 2021/0030349 A1    Feb. 4, 2021

Related U.S. Application Data

(60) Provisional application No. 62/622,481, filed on Jan. 26, 2018.

(51) Int. Cl.
*A61B 5/00*     (2006.01)
*A61B 3/00*     (2006.01)
(Continued)

(52) U.S. Cl.
CPC ............ *A61B 5/4064* (2013.01); *A61B 3/005* (2013.01); *A61B 3/0091* (2013.01); *A61B 3/113* (2013.01);
(Continued)

(58) Field of Classification Search
CPC ..... A61B 5/4064; A61B 3/005; A61B 3/0091; A61B 3/113; A61B 5/7282; A61B 3/14;
(Continued)

(56) References Cited

U.S. PATENT DOCUMENTS

2015/0245766 A1*  9/2015  Rennaker ................. A61B 3/14
                                                        351/210
2016/0278716 A1*  9/2016  Samadani .............. A61B 5/031

OTHER PUBLICATIONS

Hasegawa, Tatsuhisa, et al. "Active linear head motion improves dynamic visual acuity in pursuing a high-speed moving object." Experimental brain research 194.4 (2009): 505-516. (Year: 2009).*

(Continued)

*Primary Examiner* — David J. McCrosky
(74) *Attorney, Agent, or Firm* — SLEMAN & LUND LLP

(57) ABSTRACT

The present disclosure is directed to the first methods and systems for diagnosing a patient being affected by a brain injury from a blast with greater accuracy that previous methods. The methods and system include an automated, non-invasive method for assessing the variance of a patient's ocular motility relative to a matched cohort of unaffected subjects, and using the variance in one or more ocular motility metrics to calculate a score that indicates a likelihood that the patient suffers from a blast brain injury. The score, referred to as a BIS, discriminates between affected an unaffected subjects with a sensitivity of greater than about 85%, a specificity of greater than 75%. The ROCAUC of the BIS is greater than 0.85.

9 Claims, 9 Drawing Sheets

(51) Int. Cl.
    *A61B 3/113*     (2006.01)
    *G16H 50/20*     (2018.01)
    *G16H 50/30*     (2018.01)
    *G16H 50/50*     (2018.01)
    *G16H 50/70*     (2018.01)
    *A61B 3/14*     (2006.01)
    *G16H 10/60*     (2018.01)

(52) U.S. Cl.
    CPC ........... *A61B 5/7282* (2013.01); *G16H 50/20* (2018.01); *G16H 50/30* (2018.01); *G16H 50/50* (2018.01); *G16H 50/70* (2018.01); *A61B 3/14* (2013.01); *A61B 5/6803* (2013.01); *G16H 10/60* (2018.01)

(58) Field of Classification Search
    CPC ..... A61B 5/6803; A61B 5/163; A61B 5/7264; G16H 50/20; G16H 50/30; G16H 50/50; G16H 50/70; G16H 10/60
    See application file for complete search history.

(56) References Cited

OTHER PUBLICATIONS

Bronstein, Adolfo M., Mitesh Patel, and Qadeer Arshad. "A brief review of the clinical anatomy of the vestibular-ocular connections—how much do we know?." Eye 29.2 (2015): 163-170. (Year: 2015).*
Micromedical Technologies, Vorteq, Pamphlet. Printed Mar. 2014. (Year: 2014).*
Samadani, et al. "Eye tracking detects disconjugate eye movements associated with structural traumatic brain injury and concussion." Journal of neurotrauma 32.8: 548-556. (Year: 2015).*

* cited by examiner

Fig. 5

All patients

| | | Controls |
|---|---|---|
| N | Valid | 842 |
| | Missing | 14 |
| Mean | | 10.0233 |
| Median | | 9.7422 |
| Mode | | 0.00 |
| Range | | 100.00 |
| Minimum | | 0.00 |
| Maximum | | 100.00 |
| Sum | | 8439.66 |
| Percentiles | 10 | 0.0000 |
| | 20 | 0.0444 |
| | 25 | 0.1790 |
| | 30 | 0.6920 |
| | 40 | 6.9322 |
| | 50 | 9.7422 |
| | 60 | 11.6627 |
| | 70 | 13.6012 |
| | 75 | 14.2976 |
| | 80 | 15.0028 |
| | 90 | 17.2846 |
| Std. Error of Mean | | 0.42430 |
| Std. Deviation | | 12.3121 |
| Variance | | 151.569 |
| Skewness | | 3.860 |
| Std. Error of Skewness | | 0.084 |
| Kurtosis | | 20.546 |
| Std. Error of Kurtosis | | 0.168 |

Patients with zero prior TBIs

| | | Controls |
|---|---|---|
| N | Valid | 301 |
| | Missing | 5 |
| Mean | | 5.9757 |
| Median | | 1.9362 |
| Mode | | .00ᵃ |
| Range | | 65.01 |
| Minimum | | 0.00 |
| Maximum | | 65.01 |
| Sum | | 1798.69 |
| Percentiles | 10 | 0.0000 |
| | 20 | 0.0074 |
| | 25 | 0.0316 |
| | 30 | 0.0742 |
| | 40 | 0.4574 |
| | 50 | 1.9382 |
| | 60 | 8.3819 |
| | 70 | 9.2802 |
| | 75 | 10.2393 |
| | 80 | 11.9391 |
| | 90 | 15.3755 |
| Std. Error of Mean | | 0.44289 |
| Std. Deviation | | 7.68369 |
| Variance | | 59.042 |
| Skewness | | 2.404 |
| Std. Error of Skewness | | 0.140 |
| Kurtosis | | 12.254 |
| Std. Error of Kurtosis | | 0.280 |

GROUPED ACCORDING TO GENDER — WITH ZERO TBI

| | | Controls Gender | |
|---|---|---|---|
| | | F | M |
| N | Valid | 115 | 186 |
| | Missing | 5 | 0 |
| Mean | | 12.6806 | 1.6302 |
| Median | | 11.6818 | 0.0945 |
| Mode | | 8.36ᵃ | .00ᵃ |
| Range | | 32.27 | 65.01 |
| Minimum | | 8.36 | 0.00 |
| Maximum | | 40.63 | 65.01 |
| Sum | | 1458.27 | 340.42 |
| Percentiles | 10 | 8.7493 | 0.0000 |
| | 20 | 8.9848 | 0.0000 |
| | 25 | 9.2383 | 0.0004 |
| | 30 | 9.5816 | 0.0044 |
| | 40 | 10.2582 | 0.0298 |
| | 50 | 11.6818 | 0.0945 |
| | 60 | 13.0252 | 0.2663 |
| | 70 | 14.3689 | 0.8857 |
| | 75 | 15.1083 | 1.3115 |
| | 80 | 15.6876 | 1.7738 |
| | 90 | 17.7266 | 4.4057 |
| Std. Error of Mean | | 0.42439 | 0.4505 |
| Std. Deviation | | 4.55111 | 6.1447 |
| Variance | | 20.713 | 37.756 |
| Skewness | | 2.839 | 7.421 |
| Std. Error of Skewness | | 0.226 | 0.178 |
| Kurtosis | | 12.214 | 66.549 |
| Std. Error of Kurtosis | | 0.447 | 0.355 |

# METHODS AND KITS FOR DETECTION OF BLAST BRAIN INJURY, ITS SEVERITY, DISTANCE FROM BLAST EPICENTER, AND CLASSIFICATION RELATIVE TO THE LARGER SPECTRUM OF CONCUSSION

CROSS-REFERENCE TO RELATED APPLICATIONS

This is a National Stage of International Application No. PCT/US19/015245 filed Jan. 25, 2019, and claims priority to U.S. Provisional Patent Application Ser. No. 62/622,481, filed Jan. 26, 2018, the contents of all of which are incorporated herein by reference in their entirety as if fully set forth herein.

FIELD

The present disclosure is directed to the first methods and systems for accurately diagnosing a patient affected by a brain injury from a blast using an automated, non-invasive assessment of ocular motility. Assessment includes calculating the variance of a patient's ocular motility relative to a matched cohort of unaffected subjects (normals), displaying normal eye movement. This variance, along with various other factors, is used to calculate a score that indicates a likelihood that the patient has been affected by a blast brain injury. The score, referred to as a BIS (Blast Impact Score), can be calculated in less than about 10 minutes and discriminates between affected an unaffected subjects (normals) with a sensitivity of greater than about 85%, a specificity of greater than 75%. The ROCAUC of the BIS is greater than 0.85. Also disclosed is a BIS index for assessing the severity of a patient's injury.

BACKGROUND

Blast brain injury has been dubbed "the invisible injury" because it often does not cause immediately detectable radiographic injury, and serum or cerebrospinal fluid biomarker changes are transient. Blast exposure in military personnel causes brain injury associated with a decline in balance and equilibrium, hearing, self-reported well-being, emotional and cognitive function. Chronic consequences of blast brain injury are highly comorbid with pain, post-concussive syndrome, depression and post-traumatic stress, with symptomatic patients not necessarily improving over time. Autopsy of military personnel reporting post-traumatic stress and exposed to blast reveals astroglial scarring, which may represent at least one aspect of the pathophysiology of blast brain injury. Blast injury in non-military personnel has been characterized primarily by its surgical consequences with limited description of neurologic consequence in females or children, whose physiology may potentially render them differentially susceptible to injury.

Failure to recognize the neurologic consequences of blast may have potential longterm impact with one model describing victims as "'downplaying' their injuries and later 'detaching' themselves from friends, family, and communities, and 'denying' or being 'oblivious' to their circumstances until a 'wake-up call' pushed them to 'get help.'" A majority of military personnel with concussive blast experienced evolution rather than resolution of symptoms over 5 years from injury.

Recognizing its delayed and serious consequence, the military has screened for blast brain injury since at least 2007. It has dubbed it to be an "invisible injury" because it is difficult to detect acutely. Computed tomograph scanning is generally negative, and diffusion tensor imaging may be negative in many patients, despite the presence of white-matter changes in those with post-concussive syndrome. Cerebrospinal fluid and serum markers classically associated with traumatic brain injury are unchanged with exposure to 150 close-range howitzer or bazooka firings despite rodent studies that demonstrate serum biomarker changes after blast. Cytokine markers indicative of inflammation are also only transiently elevated in humans.

Ocular motility dysfunction has been described in blast injured military personnel both remotely after injury and acutely. Among the optometric measures disrupted acutely after blast are higher near vertical phoria, reduced negative fusional vergence break at near, receded near point of convergence, decreased stereoacuity, and reduced positive relative accommodation.

Development of an accurate, rapid, and straightforward diagnostic for blast brain injury would enable identification of injured subjects and allowing rapid intervention for prevention of repeat injury as well as development of therapeutics. Described herein is an automated eye tracking assay performed while watching a visual stimulus to detect blast brain injury.

BRIEF DESCRIPTION OF THE DRAWINGS

FIG. 5 are tables showing the differences between normal healthy uninjured subjects including those with prior TBI, healthy uninjured subjects without TBI and the patients exposed to blast in this study.

DETAILED DESCRIPTION

Figure 1:
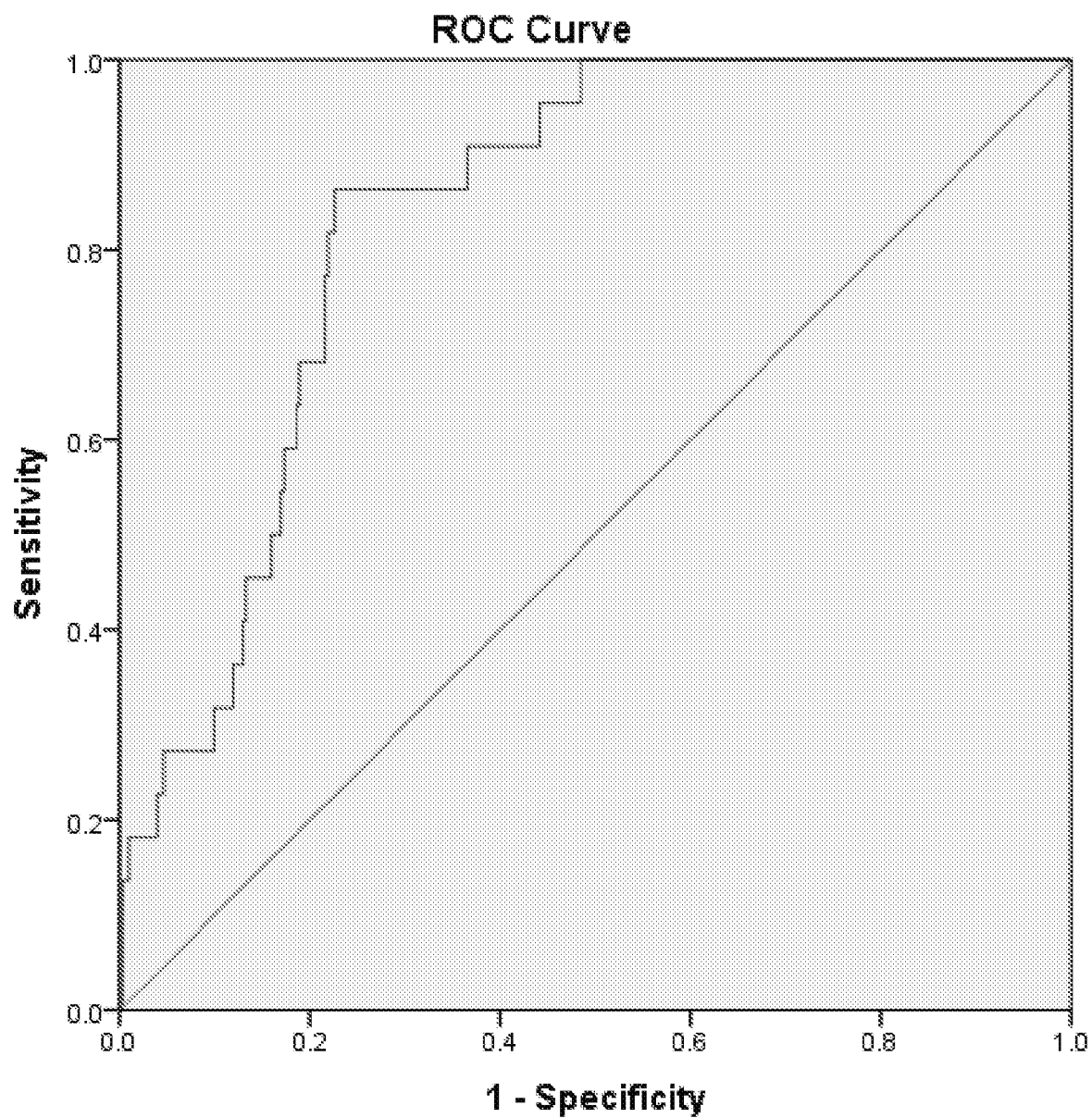
FIG. 1 depicts is a receiver operating curve (ROC) for Blast Impact Score to discriminate between blast injured subjects and individuals with no prior history of TBI. The area under the curve was 0.83
Figure 2:
FIG. 2 is a map of a blast site discussed in Examples. The triangle represents the epicenter and X's indicate the two fatalities. Circles with numbers represent BIS scores and are correlated with Table 2.

Disclosed herein are algorithms, methods, and systems for automated and non-invasive diagnosis of blast brain injury. In many embodiments, the present disclosure is directed to methods of diagnosing a blast brain injury in a patient that may have been exposed to a concussive blast. In some embodiments, the method includes measuring the eyes of a patient in response to one or more stimuli. In some embodiments, the method may include monitoring movement of the patient's eyes while the patient observes a video. In many embodiments, the patient's eye movement is measured, and an algorithm may be used to calculate a score from the one or more measurements to assess the level of neural injury.

Although gross observations of eye tracking is helpful in detecting changes in intracranial mass effect and pressure, subtle changes may be missed. Applicants have surprisingly found that automated, non-invasive eye tracking is useful in diagnosing blast brain injury. Specifically, the tracking and recording of disruptions in ocular motility, detectable by automated eye tracking devices, was identified in subjects exposed to blast. In some cases, the subjects demonstrated clinical signs and symptoms of blast brain injury. Described below in the Examples section is a prospective observational study performed with 36 predominantly female and child survivors exposed to a natural gas explosion at a school.

Ocular motility metrics can be used to determine the likelihood that a patient, or test subject, has been exposed to a blast and is suffering neural impairment. In many embodiments, a monitor displays a moving image and the patient's eye movement (monocular and/or binocular, spatial and temporal) is tracked and recorded while following the image with their eyes. The patient may be at a fixed distance from the monitor, by using supports for the patient's chin and/or forehead, or the patient's head maybe free to move. In many cases, an object is displayed within a larger viewing area, such that the patient's attention and gaze is directed to the moving object within a static field. In many embodiments, the object may be a small window, approximately ⅛ the size of the viewing area. In many embodiments, the viewing area is a monitor. The small window may play an interesting video to attract the patient's attention. The larger window may be a predominantly static, dimensionless or blank background. The small window may scribe a shape within the large window, such as a square, rectangle, polygon, circle, rhomboid, or quadrilateral. In most embodiments, the shape may be described as having two or more segments, for example a square may be defined as having segments of a top, bottom, left side, and right side, and a circle may be defined as having segments of a left half and right half, or top half and bottom half. In many embodiments, the shape may define 2, 3, 4 or more segments. In many embodiments the small window may move along the outer edges of the larger window or monitor. The ocular metrics tracked may include one or more of an area, a height, a width, a length, a radius, depth, etc. In some embodiments, where the small window scribes a box, the metrics are a box area, a box height, etc. In most embodiments, separate metrics are tracked for each of the patient's eyes (right and left). An appendix titled EyeBoxCNA Metrics ("Appendix"), attached, includes definitions and descriptions of various calculations and measurements used in some embodiments of the described methods. The disclosed definitions and descriptions are not meant to limit the scope of the presently described methods and systems. Metrics for use with the disclosed methods and systems may be any one or more of the metrics described in the Appendix, which is incorporated in its entirety. For example, the metric may be a mean, median, variance, standard deviation, skew, or normalized skew of any one or more of box height, box width, aspect ratio, box aspect ratio, box area, segment distance, conjugacy, conjugacy variance, conjugacy variance x ratio top/bottom, conjugacy variance y ratio top/bottom, conjugacy variance x ratio left/right, conjugacy variance y ratio left/right, distance in aspect ratio left/right, conjugacy variance of delta aspect, and segment velocity.

Eye tracking data collection may be efficient and rapid. In some embodiments, eye tracking data, sufficient to assess blast brain injury, may be collected for less than about 15 min., 10 min., 9 min., 8 min., 7 min., 6 min., 5 min., 4 min., 3 min., 2 min., or 1 min., and more than about 30 seconds, 1 min., 2 min., 3 min., 4 min., 5 min., 6 min., 7 min., 8 min., 9 min., or 10 min. In many embodiments, a patient's eye movement is tracked over about 2.5 minutes.

A patient's or test subject's ocular metrics may be compared to those of a matched population of control subjects. In many embodiments, the control subjects may have no history of concussive brain injury and may possess demographic characteristics matching the patient. In some embodiments, the characteristics may include age and gender. In many embodiments, the variance of the patient's metrics, relative to the control subjects' may be calculated. Variances of any one or more of the metrics described at the Appendix may be calculated. In some embodiments the calculated variance may include one or more of total left eye, total right eye, and conjugate movement, box area, box height, etc. In many embodiments, the calculated variance is conjvarXtop (see, e.g. equation 109 of Appendix).

The likelihood that a subject has been exposed to a blast may be expressed as a number or score—the Blast Impact Score (BIS). The BIS may be calculated based on age, gender, and variance from one or more of the measured metrics. In many embodiments, the metric included in the BIS is conjvarXtop. In many embodiments the BIS equation is:

A high BIS may indicate exposure to a blast and the presence of a traumatic brain injury. In many embodiments a BIS of greater than or equal to about 10.75 may be considered positive for blast injury, and higher BIS values indicate more severe injury.

In some embodiments, the ROCAUC, sensitivity, and specificity of the BIS for discriminating between blast patients and controls is high. In many embodiments, the BIS may have an ROCAUC of greater than about 0.60, 0.65, 0.70, 0.75, 0.80, 0.85, 0.90, 0.95, and 0.0975, and less than about 0.995, 0.95, 0.90, 0.85, 0.80, 0.75, 0.70, 0.65, and 0.60. In some preferred embodiments, the BIS may result in an ROCAUC of about 0.835. In some embodiments, the sensitivity of the BIS may be greater than about 60%, 65%, 70%, 75%, 80%, 85%, 90%, 95%, or 97%, and less than about 100%, 95%, 90%, 85%, 80%, 75%, 70%, 65%, or 60%. In some preferred embodiments the sensitivity is about 86.4%. In some embodiments, the specificity of the BIS may be greater than about 60%, 65%, 70%, 75%, 80%, 85%, 90%, 95%, or 97%, and less than about 100%, 95%, 90%, 85%, 80%, 75%, 70%, 65%, or 60%. In some preferred embodiments the sensitivity is about 77.4%.

The BIS may also correlate with a patient's distance from a blast epicenter. In some embodiments, the BIS correlation with distance from the blast epicenter is greater than about 0.6, 0.7, or 0.8, for example about 0.731.

In many embodiments, detection of blast brain injury using the disclosed automated non-invasive techniques, methods, and systems may enable early identification of subjects affected by a blast injury. This identification may be useful in protecting a patient from repeated exposure and/or in developing therapeutics to treat blast brain injury patients.

Figure 3:
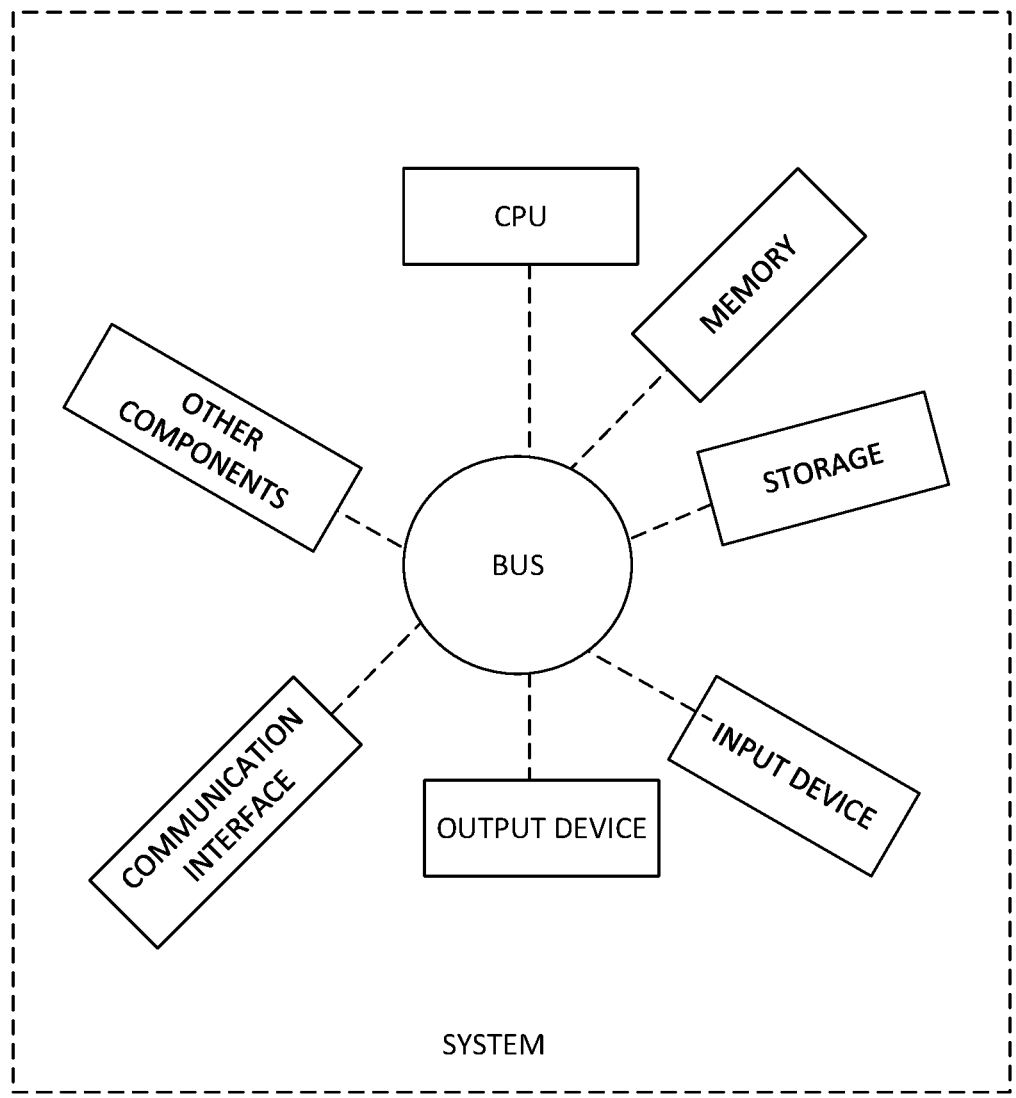
FIG. 3 is a diagram of one embodiment of a computer system for use with the disclosed algorithms, methods, and systems.

The disclosed algorithms, methods, and systems may be implemented in a digital computer system. One embodiment of such a system is shown in FIG. 3. Such a digital computer is well-known in the art and may include one or more of a central processing unit, one or more of memory and/or storage, one or more input devices, one or more output devices, one or more communications interfaces, and a data bus. In some embodiments, the memory may be RAM, ROM, hard disk, optical drives, removable drives, etc. In some embodiments, storage may also be included in the disclosed system. In some embodiments, storage may resemble memory that may be remotely integrated into the system.

The disclosed system may further include at least one output device, for example one or more monitors, display units, video hardware, printers, speakers, etc. In most embodiments, at least one output device is a monitor for viewing the diagnostic video. One or more input devices may also be included, for example pointing devices (e.g., mouse), text input devices (e.g., keyboard), touch screen, cameras, etc. In most embodiments, at least one input device is a camera for monitoring the patient's eye movement. In some embodiments the camera may be a webcam. In various embodiments, the camera may be part of a wearable device, for example a helmet or goggle. In further embodiments, the helmet or goggle may also include one or more display devices such as screens, projectors, monitors, or other device.

The disclosed system may further include at least one communications interfaces, such as LAN network adapters, WAN network adapters, wireless interfaces, Bluetooth interfaces, modems and other networking interfaces.

The disclosed system may further include one or more data buses for communication among the various parts of the disclosed system, for example input/output buses and bus controllers.

In some embodiments, the disclosed system may comprise one or more distributed computers, and may be implemented in various types of software languages including, without limitation C, C++, COBOL, Java, FORTRAN, Python, Pascal, among others. The skilled artisan may compile various software source codes into executable software for use with the disclosed system.

Figure 4:
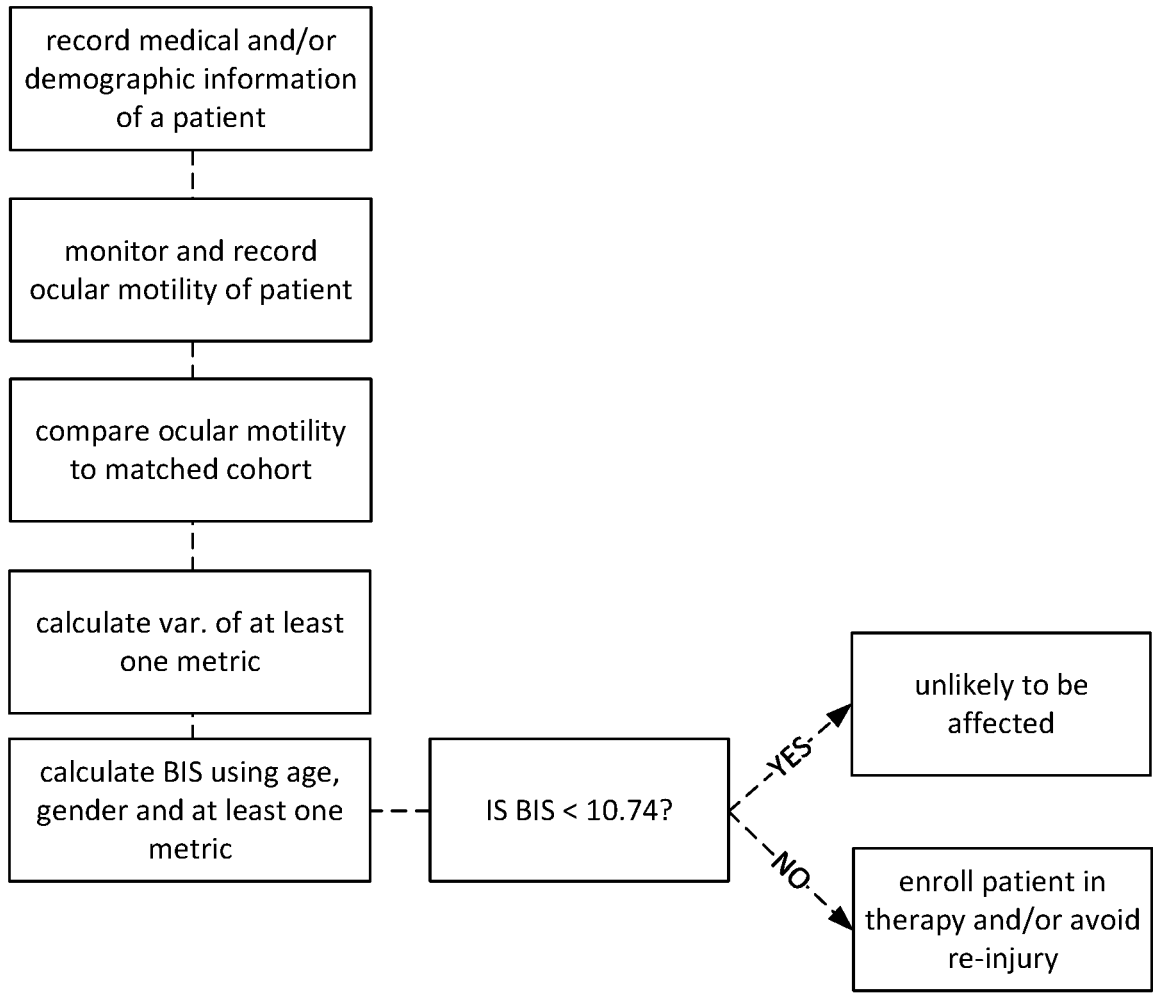
FIG. 4 is a diagram outlining steps involved in one embodiment of the disclosed methods.
Figure 6:
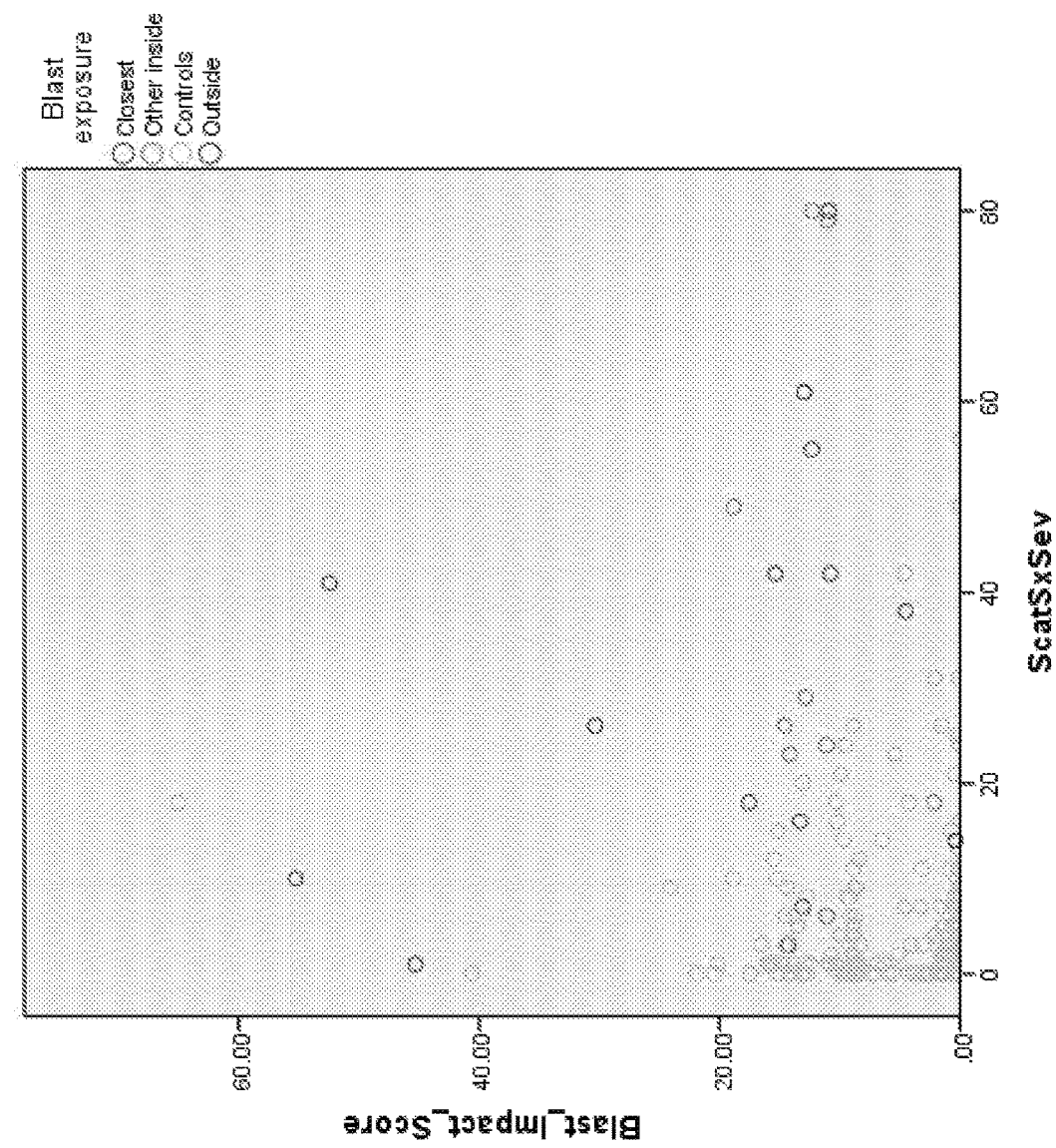
FIG. 6 is a scatter plot showing Blast Impact Scale score versus symptom severity as tested by the Sport Concussion Assessment Tool. Distance from the blast is indicated by the type of circle.
Figure 7:
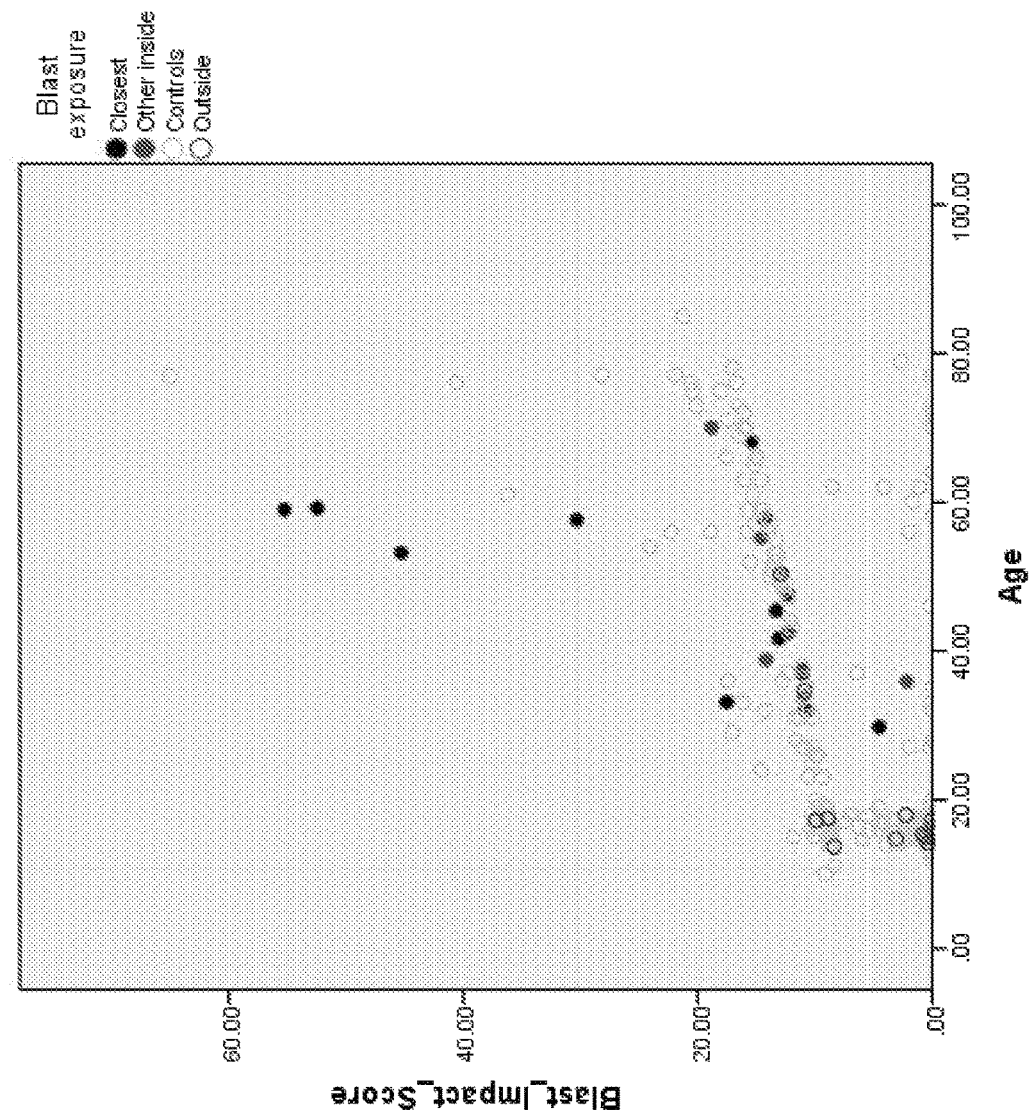
FIG. 7 is a scatter plot showing Blast Impact Scale score versus age. Distance from the blast is indicated by the type of circle.
Figure 8:
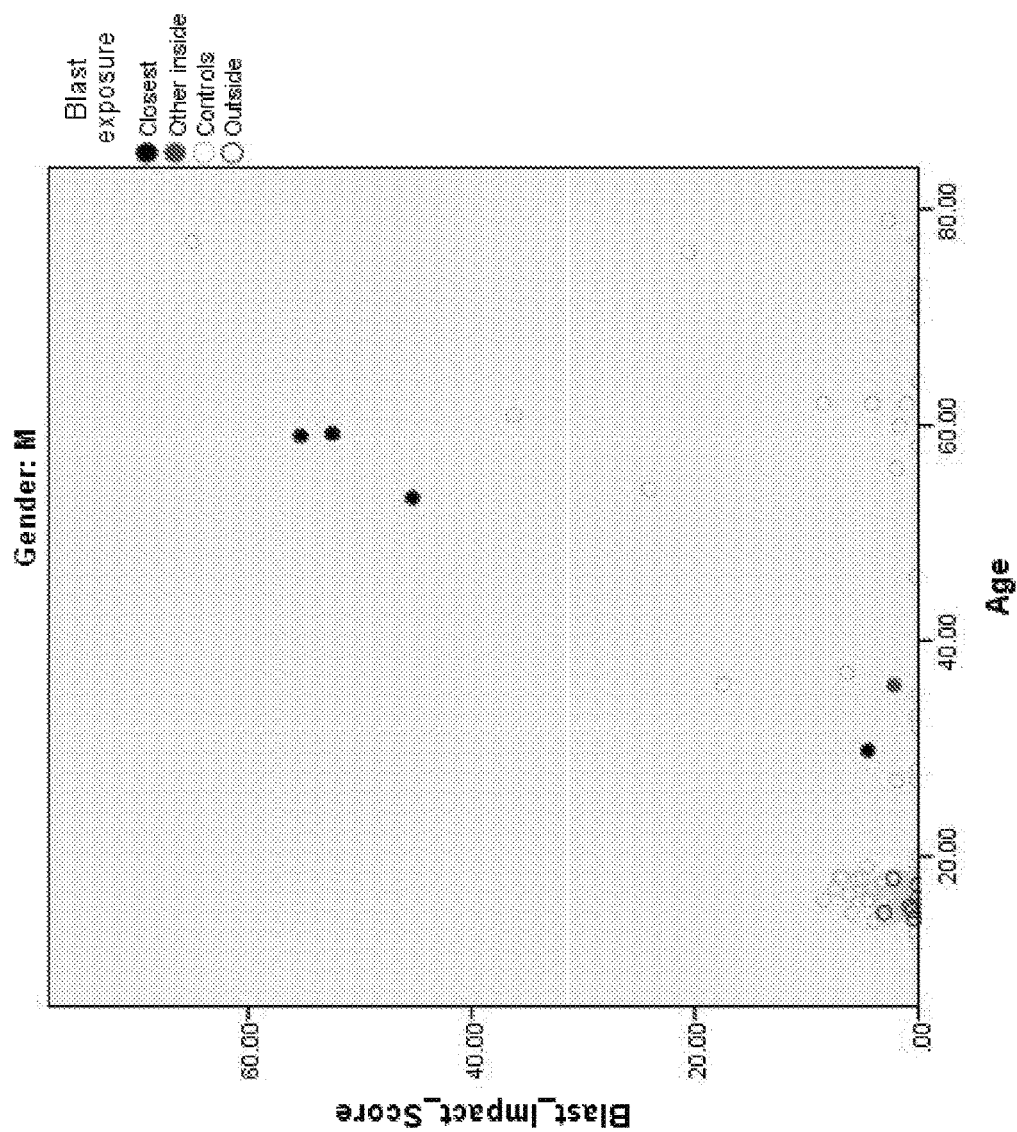
FIG. 8 is a scatter plot showing Blast Impact Scale score versus age for males. Distance from the blast is indicated by the type of circle.
Figure 9:
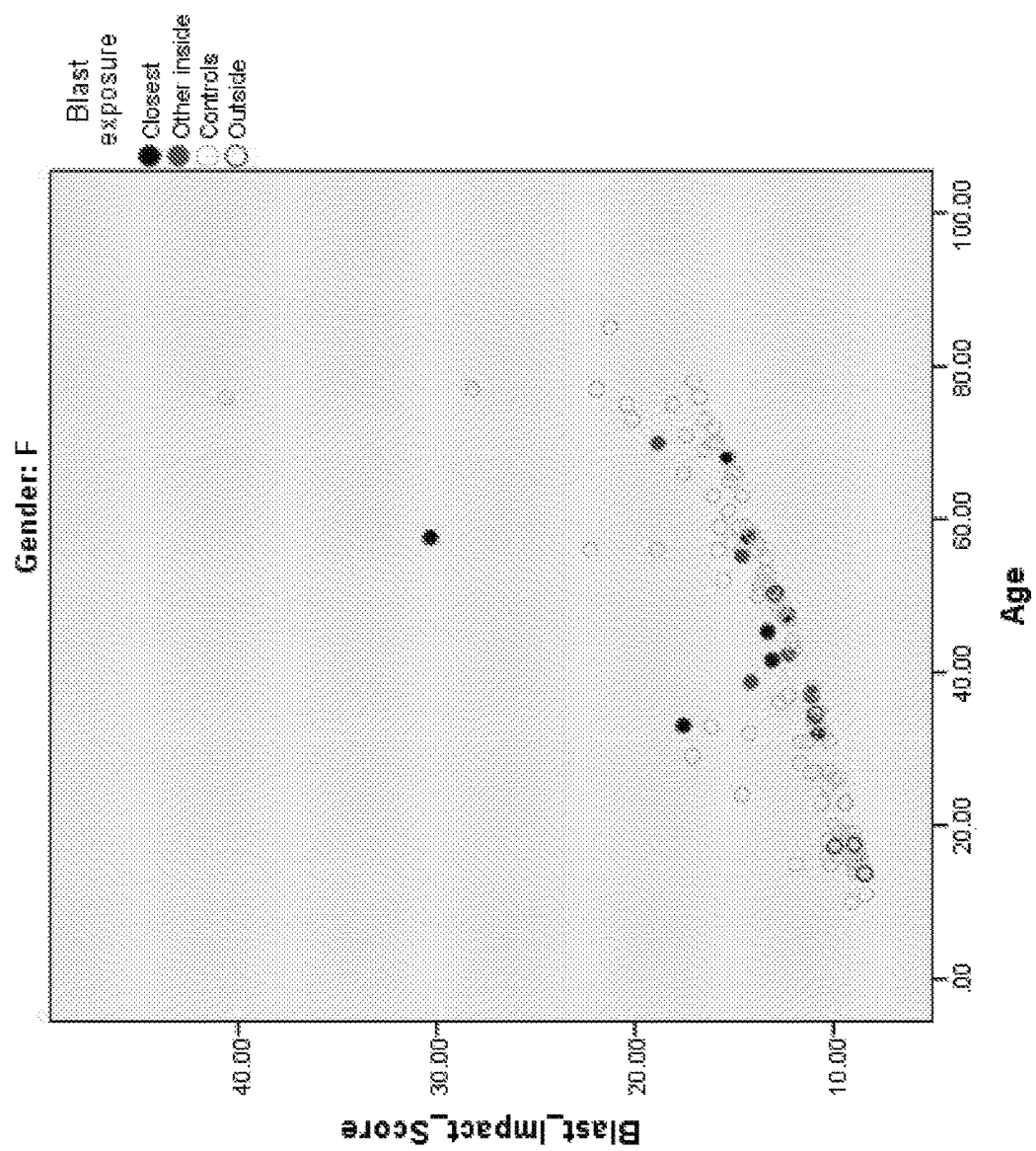
FIG. 9 is a scatter plot showing Blast Impact Scale score versus age for males. Distance from the blast is indicated by the type of circle.

FIG. 4 shows a flowchart for one embodiment of the disclosed system. In this method, a patient is identified as a candidate for testing; the patient's ocular motility is analyzed and values are recorded; the patient's recorded values are then compared with an age and gender matched cohort of unaffected subjects (normals); the variance of the patient's values, relative the cohort's is calculated for at least one metric; an algorithm of the present disclosure is used to calculate a BIS using the patient's age, gender, and at least one metric variance; if the calculated BIS is less than about 10.75 the patient does not have blast brain injury; if the BIS value is greater than about 10.75 the patient is advised to start therapy and or avoid re-injury.

EXAMPLES

Example 1

Approximately 70 civilian children and adults were accidently exposed to a natural gas explosion at a school. Two people died at the scene and six were evaluated at the hospital. 36 subjects, including 4 of those that were hospitalized agreed to participate in this research. These blast subjects were compared to an age and gender matched cohort selected from among 561 controls recruited at a state fair.

Automated eye tracking metrics were measured, along with near point of convergence, binocular amplitude of accommodation, and SCAT3 subsets.

Methods:

This research received IRB approval and written informed consent was obtained from every participant or their guardian, as well as assent from children under the age of 18 years.

1. Inclusion and Exclusion Criteria

Blast survivors were enrolled in the study either if they expressed interest when offered participation during assessment of blast injury in the hospital, or if they volunteered after hearing an informational discussion about blast brain injury presented two days after the explosion. All noted experiencing blast overpressure wave impact at the time of the explosion. Pertinent ophthalmologic and neurologic medical history was obtained. One survivor was excluded due to extensive comorbid conditions precluding opening of eyes.

Controls were recruited at a State Fair Booth entitled "Healthy Brain Initiative." People passing by were advised that the purpose of the research being conducted was to assess brain injury history and impact. Interested subjects were invited to participate in any portion of the study (brain injury history screening, eye tracking, Sports Concussion Assessment Tool-V3 [SCAT3] and/or NIH toolbox assessments) after informed consent was obtained.

2. Concussion Assessment and Eye Tracking

Blast survivors were assessed with subsets of the SCAT-3: the Glasgow coma scale (GCS); the Total Number of Symptoms (TNS) and Symptom Severity Score (SSS) from the Symptom Checklist (SC); and the Standardized Assessment of Cognition (SAC). Near point of convergence was assessed by asking the patient to focus on a letter in the 20/30 column of print of the Logarithm of the Minimum Angle of Resolution (log MAR) text that was slowly moved on a convergence ruler from 40 cm from the eyes toward the patient's face. The point at which the patient saw blurry was recorded in centimeters as binocular amplitude of accommodation (BAA). The text was then moved forward from the BAA until the letter appears double. The distance from the face is measured in centimeters and recorded as the near point of convergence (NPC).

Eye tracking was performed with an Eyelink 1000 eye tracker at a fixed distance of 55 cm from a computer monitor over a time period of 220 seconds. The distance was fixed by means of a chinrest attached to the base of the viewing monitor and camera. Each subject was seated and the monitor height was adjusted to the subject's chin. The visual stimuli were the music videos Shakira Waka-Waka or K'naan Wavin' Flag, Tennessee NCAA football history, Top Gear clip of Ferrari, or Disney videos. The video was played continuously in a square aperture with an area approximately ⅛ the screen size while moving clockwise along the outer edges of a rectangular (aspect ratio 4:3) viewing monitor at a rate of 10 s per side for five complete cycles of 40 s each. Participants under 18 were shown the DISNEY videos from Puss in Boots and the Lion King exclusively.

3. Statistics

Statistical analyses were carried out using Statistical Package for the Social Sciences (SPSS statistics version 24, IBM Corporation, Armonk, NY). Descriptive statistics for age and gender were calculated for each group. Exploratory data analysis was conducted by creating scatter plots for eye tracking metrics, Symptom Severity Score (SSS) from the SCAT3 symptom checklist and the group of patients. An age and gender matched sample was then pulled out of the controls and differences in eye tracking metrics between controls and blast subjects were tested using Wilcoxon signed-rank test that allows for testing between the paired data with non-normal distribution.

A model, blast impact score (BIS), was then created using multiple logistic regression, while adjusting for age and gender to predict the impact of the blast. The subjects indoors at the time of blast were compared to controls with no prior history of TBI. Area under the receiver operating curve, sensitivity and specificity of the model were calculated to appraise the model accuracy.

The model was then further tested on all the blast subjects against their distance from the blast site. We treated distance as a four-level ordinal variable that took into account the distance of the person and whether or not person was indoors. The levels were (1) indoors and closest to the epicenter of the blast, (2) indoors but further away from the blast, (3) outdoors and exposed to the blast and (4) non-blast-exposed controls. Spearman correlation was used to test the association between BIS and severity of exposure to the blast. Finally, in order to depict results in an easy to understand fashion, we created a map with the BIS for each subject corresponding to his/her location.

Results:

Six blast survivors were brought to the hospital. One had a GCS of 6 and was intubated and underwent emergent surgery for orthopedic and vascular injuries. The remaining five all had a GCS of 15, with only one of these five reporting a transient loss of consciousness at the scene. Other neurologic symptoms reported were headache, scalp pain due to a laceration, dizziness and anxiety in one patient each. Of these five patients, two were recruited for concussion assessment and eye tracking on the day of injury, and two returned for assessment in the ensuing days. The fifth declined research participation.

An additional 32 survivors denied loss of consciousness or neurologic injury at the scene, but presented to the laboratory for assessment in days 3-9 after the explosion.

Thirty-six blast exposed subjects [age (mean±sd)=35.6±17.5, range 13-70 years, 23 females] who underwent assessment at the laboratory using eye tracking were compared using Wilcoxon signed-rank test to thirty-six age and gender matched controls obtained from a total of 574 community controls not exposed to blast [age (mean±sd)=48.2±19.6, range 5-90 years, 388 females]. Five eye tracking metrics were significantly different between blast survivors and age and gender matched randomly selected controls. These metrics included median box height (left eye) (p=0.018), left var Xleft (p=0.029), right var X left (p=0.030), left box area (0.035) and right box area (0.048) (Table 1). Survivors who were indoors in greatest proximity to the blast (N=12; (mean±sd)=48.7±12.5, range 30-68, 8 females) had the most significant differences in left eye total variance (p=0.016), right eye total variance (p=0.016) and conj var Y bot (p=0.028) metrics (table 2). Left var Xleft also correlated with symptom severity (spearman's correlation coefficient=0.433). The two clinical measures of clinical oculomotor dysfunction, near point of convergence and binocular amplitude of accommodation, were not significantly different in blast exposed patients versus their age and gender matched controls (p=0.582 and 0.859 respectively).

TABLE 1

Blast impact score—model parameters

| Parameters | Estimate | SE | t-Stat | p-Value |
|---|---|---|---|---|
| Intercept | −2.56913 | 0.60161 | −4.27043 | 1.95E−05 |
| Age | 0.012456 | 0.012684 | 0.98209 | 0.326055 |
| Gender (male) | −0.51737 | 1.40563 | −0.36807 | 0.712819 |
| Conj varXtop | 16.57131 | 19.18878 | 0.863594 | 0.387811 |
| Age and Gender (male) interaction | 0.057695 | 0.027348 | 2.10963 | 0.03489 |
| Gender (male) and conjvarXtop interaction | −2060.8 | 1011.02 | −2.03834 | 0.041516 |

In order to create a model to predict the severity of blast, subjects inside the building [N=22; 17 females] were compared to controls with no prior history of TBI [N=306; 120 females] using logistic regression. The resulting model yielded a score, Blast impact score (BIS) that can be depicted as follows:

$$\text{Blast\_Impact\_Score} = \exp(y)/(1+\exp(y)) * 100$$

Where:
$y = -2.569133882 + 0.01245639*\text{age} - 0.517373229*\text{gender} + 16.57131011*\text{conjvarXtop} + 0.057694955*\text{age}*\text{gender} - 2060.801989*\text{gender}*\text{conjvarXtop}$ Gender would be 1 if male, zero if female. The resulting BIS will be considered positive for blast injury if greater than or equal to 10.75. Higher numbers indicate worse BIS. Further model details are listed in Table 1 below.

BIS provided an AUC of 0.835 (95% C.I.=0.773 to 0.897; FIG. 1), sensitivity of 86.4% and specificity of 77.4% to discriminate between blast patients and controls. BIS also correlated with distance from the epicenter of the blast (spearman correlation=0.731; p-value <0.001; FIG. 1, Table 3), with highest levels noted in individuals inside, closest to the blast, then inside but away from the blast, and then outside exposed to the blast.

TABLE 2

Individuals with blast ranked in order of Blast Impact Score (BIS). The table provides values for binocular amplitude of accommodation (BAA), Near point of convergence (NPC), symptom severity score SSS, standardized assessment of cognition SAC, total number of symptoms (TNS) and days between blast and assessment. Map ID refers to identification numbers in FIG. 1.

| Map ID | Box score | BAA | NPC | SSS | SAC | TNS | Days | BIS |
|---|---|---|---|---|---|---|---|---|
| 55 | 15.9 | 28 | 9 | 10 | 5 | 5 | 0 | 55 |
| 52 | 16.5 | 7 | 5 | 41 | 29 | 17 | 8 | 52 |
| 45 | 2.0 | 29 | 17 | 1 | 29 | 1 | 8 | 45 |
| 30 | 18.6 | 14 | 7 | 26 | 26 | 12 | 6 | 30 |
| 19 | 18.0 | N/a | N/a | 49 | 27 | 15 | 7 | 19 |
| 18 | 4.9 | 12 | 4 | 18 | 28 | 10 | 5 | 18 |
| 15a | 19.3 | 12 | 8 | 42 | 27 | 18 | 4 | 15 |
| 15b | 5.1 | 29 | 9 | 26 | 27 | 9 | 6 | 15 |
| 14a | 11.9 | 28 | 0 | 3 | 28 | 2 | 6 | 14 |
| 14b | 16.0 | 15 | 5 | 23 | 29 | 7 | 7 | 14 |
| 13a | 7.2 | 8 | 3 | 7 | 27 | 5 | 4 | 13 |
| 13b | 13.4 | 18 | 2 | 16 | 29 | 9 | 6 | 13 |
| 13c | 3.6 | 26 | 7 | 29 | 25 | 15 | 7 | 13 |
| 13d | 3.6 | 33 | 26 | 61 | 23 | 19 | 8 | 13 |
| 12 | 5.7 | 14 | 8 | 80 | 23 | 20 | 6 | 12 |
| 12 | 13.7 | 24 | 6 | 61 | 5 | 17 | 0 | 12 |
| 11a | 3.5 | 29 | 21 | 42 | 25 | 14 | 4 | 11 |
| 11b | 10.4 | 13 | 8 | 6 | 26 | 6 | 5 | 11 |
| 11c | 2.5 | 25 | 5 | 79 | 25 | 18 | 6 | 11 |
| 11d | 2.5 | 20 | 10 | 24 | 28 | 11 | 7 | 11 |
| 11e | 2.4 | 19 | 4 | 80 | 26 | 21 | 8 | 11 |
| 10 | 8.4 | 6 | 2 | 8 | 29 | 8 | 6 | 10 |
| 9a | 5.8 | 8 | 7 | 8 | 26 | 7 | 6 | 9 |
| 9b | 2.2 | 5 | 2 | 7 | 28 | 6 | 7 | 9 |

TABLE 2-continued

Individuals with blast ranked in order of Blast Impact Score (BIS). The table provides values for binocular amplitude of accommodation (BAA), Near point of convergence (NPC), symptom severity score SSS, standardized assessment of cognition SAC, total number of symptoms (TNS) and days between blast and assessment. Map ID refers to identification numbers in FIG. 1.

| Map ID | Box score | BAA | NPC | SSS | SAC | TNS | Days | BIS |
|---|---|---|---|---|---|---|---|---|
| 8 | 5.8 | 24 | 19 | 0 | 25 | 0 | 7 | 8 |
| 4 | 1.8 | 15 | 10 | 38 | 27 | 16 | 9 | 4 |
| 3 | 3.4 | 9 | 6 | 1 | 30 | 1 | 7 | 3 |
| 2a | 1.4 | 6 | 4 | 3 | 28 | 3 | 3 | 2 |
| 2b | 3.4 | 10 | 8 | 18 | 25 | 7 | 7 | 2 |
| 1a | 4.3 | 10 | 3 | 8 | 27 | 5 | 7 | 1 |
| 1b | 2.4 | 13 | 4 | 3 | 28 | 3 | 8 | 1 |
| 0a | 15.3 | 7 | 3 | 15 | 29 | 11 | 3 | 0 |
| 0b | 7.8 | 2 | 0 | 2 | 26 | 2 | 5 | 0 |
| 0c | 2.7 | 9 | 9 | 10 | 27 | 6 | 8 | 0 |
| 0d | 2.1 | 9 | 7 | 14 | 28 | 6 | 5 | 0 |

Discussion

Blast brain injury causes elevated ICP in humans and in animal models[29] [30]. One rat model demonstrated increases in ICP at 1-3 hours and then 2 days after the blast[31]. Humans exposed to blast may therefore have eye tracking changes that correlate with elevated ICP[27]. Two of the metrics impacted by changes in ICP, right and left box area, were disrupted in the blast survivors relative to age and gender matched controls.

REFERENCES

Akin F W, Murnane O D. Head injury and blast exposure: vestibular consequences. Otolaryngol Clin North Am 2011; 44(2):323-34, viii.

Wares J R, Hoke K W, Walker W, et al. Characterizing effects of mild traumatic brain injury and posttraumatic stress disorder on balance impairments in blast-exposed service members and Veterans using computerized posturography. J Rehabil Res Dev 2015; 52(5):591-603.

Karch S J, Capo-Aponte J E, McIlwain D S, et al. Hearing Loss and Tinnitus in Military Personnel with Deployment-Related Mild Traumatic Brain Injury. US Army Med Dep J 2016 (3-16):52-63.

Heltemes K J, Holbrook T L, Macgregor A J, et al. Blast-related mild traumatic brain injury is associated with a decline in self-rated health amongst US military personnel. Injury 2012; 43(12):1990-5.

Agoston D V, Kamnaksh A. Modeling the Neurobehavioral Consequences of Blast-Induced Traumatic Brain Injury Spectrum Disorder and Identifying Related Biomarkers. In: Kobeissy F H, ed. Brain Neurotrauma: Molecular, Neuropsychological, and Rehabilitation Aspects. Boca Raton (Fla.), 2015.

Couch J R, Stewart K E. Headache Prevalence at 4-11 Years After Deployment-Related Traumatic Brain Injury in Veterans of Iraq and Afghanistan Wars and Comparison to Controls: A Matched Case-Controlled Study. Headache 2016; 56(6):1004-21.

Walker W C, Franke L M, Sima A P, et al. Symptom Trajectories After Military Blast Exposure and the Influence of Mild Traumatic Brain Injury. J Head Trauma Rehabil 2017; 32(3):E16-E26.

Shively S B, Horkayne-Szakaly I, Jones R V, et al. Characterisation of interface astroglial scarring in the human brain after blast exposure: a post-mortem case series. The Lancet Neurology 2016; 15(9):944-53.

Jaffe D H, Peleg K, Israel Trauma G. Terror explosive injuries: a comparison of children, adolescents, and adults. Annals of surgery 2010; 251(1):138-43.

Sandvall B K, Jacobson L, Miller E A, et al. Fireworks type, injury pattern, and permanent impairment following severe fireworks-related injuries. Am J Emerg Med 2017.

Chase R P, McMahon S A, Winch P J. Injury careers after blast exposure among combat veterans deployed to Iraq or Afghanistan. Soc Sci Med 2015; 147:309-16.

Mac Donald C L, Barber J, Jordan M, et al. Early Clinical Predictors of 5-Year Outcome After Concussive Blast Traumatic Brain Injury. JAMA neurology 2017; 74(7): 821-29.

DePalma R G, Hoffman S W. Combat blast related traumatic brain injury (TBI): Decade of recognition; promise of progress. Behav Brain Res 2016.

Mac Donald C L, Johnson A M, Cooper D, et al. Detection of blast-related traumatic brain injury in U.S. military personnel. The New England journal of medicine 2011; 364(22):2091-100.

Miller D R, Hayes J P, Lafleche G, et al. White matter abnormalities are associated with chronic postconcussion symptoms in blast-related mild traumatic brain injury. Hum Brain Mapp 2016; 37(1):220-9.

Blennow K, Jonsson M, Andreasen N, et al. No neurochemical evidence of brain injury after blast overpressure by repeated explosions or firing heavy weapons. Acta Neurol Scand 2011; 123(4):245-51.

Ahmed F, Plantman S, Cernak I, et al. The Temporal Pattern of Changes in Serum Biomarker Levels Reveals Complex and Dynamically Changing Pathologies after Exposure to a Single Low-Intensity Blast in Mice. Front Neurol 2015; 6:114.

Liu M D, Luo P, Wang Z J, et al. Changes of serum Tau, GFAP, TNF-alpha and malonaldehyde after blast-related traumatic brain injury. Chin J Traumatol 2014; 17(6):317-22.

Gill J, Motamedi V, Osier N, et al. Moderate blast exposure results in increased IL-6 and TNFalpha in peripheral blood. Brain Behav Immun 2017; 65:90-94.

Cifu D X, Hoke K W, Wetzel P A, et al. Effects of hyperbaric oxygen on eye tracking abnormalities in males after mild traumatic brain injury. J Rehabil Res Dev 2014; 51(7): 1047-56.

Magone M T, Kwon E, Shin S Y. Chronic visual dysfunction after blast-induced mild traumatic brain injury. J Rehabil Res Dev 2014; 51(1):71-80.

Capo-Aponte J E, Tarbett A K, Urosevich T G, et al. Effectiveness of computerized oculomotor vision screening in a military population: pilot study. J Rehabil Res Dev 2012; 49(9):1377-98.

Goodrich G L, Flyg H M, Kirby J E, et al. Mechanisms of TBI and visual consequences in military and veteran populations. Optom Vis Sci 2013; 90(2):105-12.

Capo-Aponte J E, Urosevich T G, Temme L A, et al. Visual dysfunctions and symptoms during the subacute stage of blast-induced mild traumatic brain injury. Military medicine 2012; 177(7):804-13.

Capo-Aponte J E, Jorgensen-Wagers K L, Sosa J A, et al. Visual Dysfunctions at Different Stages after Blast and Non-blast Mild Traumatic Brain Injury. Optom Vis Sci 2017; 94(1):7-15.

Samadani U, Farooq S, Ritlop R, et al. Detection of third and sixth cranial nerve palsies with a novel method for eye tracking while watching a short film clip. J Neurosurg 2015; 122(3):707-20.

Kolecki R, Dammavalam V, Bin Zahid A, et al. Elevated intracranial pressure and reversible eye-tracking changes detected while viewing a film clip. J Neurosurg 2017:1-8.

Samadani U, Ritlop R, Reyes M, et al. Eye tracking detects disconjugate eye movements associated with structural traumatic brain injury and concussion. J Neurotrauma 2015; 32(8):548-56.

Kawoos U, Gu M, Lankasky J, et al. Effects of Exposure to Blast Overpressure on Intracranial Pressure and Blood-Brain Barrier Permeability in a Rat Model. PLoS One 2016; 11(12):e0167510.

Feng K, Zhang L, Jin X, et al. Biomechanical Responses of the Brain in Swine Subject to Free-Field Blasts. Front Neurol 2016; 7:179.

Kawoos U, Meng X, Huang S M, et al. Telemetric intracranial pressure monitoring in blast-induced traumatic brain injury. IEEE Trans Biomed Eng 2014; 61(3):841-7.

APPENDIX—EYEBOXCNS METRICS

1 General Definitions

Raw x and y cartesian coordinates of pupil position are collected and stored in a one-dimensional vector:

$$x_i \qquad (1)$$

$$y_i \qquad (2)$$

Raw velocities of pupil along x and y axis are collected and stored in a one-dimensional vectors u and v respectively as shown below:

$$u_i \qquad (3)$$

$$v_i \qquad (4)$$

This data is normalized according to the following form:

$$\bar{x}_i = \frac{x_i - \text{Mean}(x)}{\sigma_x} \qquad (5)$$

$$\bar{y}_i = \frac{y_i - \text{Mean}(y)}{\sigma_y} \qquad (6)$$

$$\bar{u}_i = \frac{u_i - \text{Mean}(u)}{\sigma_u} \qquad (7)$$

$$\bar{v}_i = \frac{v_i - \text{Mean}(v)}{\sigma_v} \qquad (8)$$

Index i corresponds to an individual data point. The size of i depends on the eye tracking hardware capture frequency and the time of tracking. The distance between each of these points can be calculated as:

$$D_i = \sqrt{(\bar{x}_i - \bar{x}_{i-1})^2 + (\bar{y}_i - \bar{y}_{i-1})^2} \qquad (9)$$

The velocity of the pupil during that interval can be calculated as:

$$V_i = \sqrt{(\bar{u}_i - \bar{u}_{i-1})^2 + (\bar{v}_i - \bar{v}_{i-1})^2} \qquad (10)$$

The data is then sorted by eye (j=1:2, left, right), cycle (current stimulus method features an aperture that moves around the computer screen for five cycles) (k=1:5, first, second, third, fourth, fifth) and box segment (l=1:4, top, right, bottom, left). Implicit, is that each j, k, l has its own data points, n, who's size is also governed by the hardware tracking frequency and time length.

$$\bar{x}_i \rightarrow \bar{x}_{j,k,l} \qquad (11)$$

$$\bar{y}_i \rightarrow \bar{y}_{j,k,l} \qquad (12)$$

$$\bar{u}_i \rightarrow \bar{u}_{j,k,l} \qquad (13)$$

$$\bar{v}_i \rightarrow \bar{v}_{j,k,l} \qquad (14)$$

$$D_i \rightarrow D_{j,k,l} \qquad (15)$$

$$V_i \rightarrow V_{j,k,l} \qquad (16)$$

1.1 Average Cycle

An average cycle x', y', u' and v' can be computed by averaging the values for all five cycles:

$$x'_{j,l} = \frac{\sum_{k=1}^{5} x_{j,k,l}}{5} \qquad (17)$$

$$y'_{j,l} = \frac{\sum_{k=1}^{5} y_{j,k,l}}{5} \qquad (18)$$

$$u'_{j,l} = \frac{\sum_{k=1}^{5} u_{j,k,l}}{5} \qquad (19)$$

$$v'_{j,l} = \frac{\sum_{k=1}^{5} v_{j,k,l}}{5} \qquad (20)$$

This corresponds to the arithmetic average of the five cycles k.

2 Individual Metrics

2.1 Segment Mean $$\bar{x}_{j,k,l}, \qquad (21)$$

$$\bar{y}_{j,k,l}. \qquad (22)$$

Corresponds to the arithmetic average of all data points on each segment l for all j, k. The result is one number representing each segment l.

2.2 Segment Median $$\bar{\bar{x}}_{j,k,l}, \qquad (23)$$

$$\bar{\bar{y}}_{j,k,l}. \qquad (24)$$

Corresponds to the statistical median of all data points on each segment l for all j,k. The result is one number representing each segment l.

2.3 Segment Variance $$\text{Var}(\bar{x}_{j,k,l}) \qquad (25)$$

$$\text{Var}(\bar{y}_{j,k,l}) \qquad (26)$$

$$\text{Var}(\bar{u}_{j,k,l}) \qquad (27)$$

$$\text{Var}(\bar{v}_{j,k,l}) \qquad (28)$$

Corresponds to the statistical variance of all data points on each segment l for all j, k. The result is one number representing each segment l. It can also be computed for the average cycle as well.

$$\text{Var}(x_{j,k}') \qquad (29)$$

Var($y_{j,l}'$)     30

Var($u_{j,l}'$)     31

Var($v_{j,l}'$)     32

2.3.1 Specific Metrics

L.var Ytop=Var($y_{1,1}'$)     33

R.var Ytop=Var($y_{2,1}'$)     34

L.var Ybot=Var($y_{1,3}'$)     35

R.var Ybot=Var($y_{2,3}'$)     36

L.var Xrit=Var($x_{1,2}'$)     37

R.var Xrit=Var($x_{2,2}'$)     38

L.var Xlef=Var($x_{1,4}'$)     39

R.var Xlef=Var($x_{2,4}'$)     40

$$L.\ varTotal = \frac{\sum_{l=1}^{4} \text{Var}(x_{1,l}')}{4} + \frac{\sum_{l=1}^{4} \text{Var}(y_{1,l}')}{4} \quad 41$$

$$R.\ varTotal = \frac{\sum_{l=1}^{4} \text{Var}(x_{2,l}')}{4} + \frac{\sum_{l=1}^{4} \text{Var}(y_{2,l}')}{4} \quad 42$$

2.4 Segment Standard Deviation $\sigma_{\overline{x_{j,k,l}}}$,     43

$\sigma_{\overline{y_{j,k,l}}}$.     44

Corresponds to the statistical standard deviation of all data points on each segment l for all j,k. The result is one number representing each segment l.

2.5 Segment Skew

Skew($\overline{x_{j,k,l}}$)=$\overline{\overline{x_{j,k,l}}} - \widetilde{\widetilde{x_{j,k,l}}}$,     45

Skew($\overline{y_{j,k,l}}$)=$\overline{\overline{y_{j,k,l}}} - \widetilde{\widetilde{y_{j,k,l}}}$.     46

Skewness here does not correspond to the statistical skew. Skewness here calculates 'how far the mean is from the median' of all data points on each segment l for all j,k. The result is one number representing each segment l.

2.5.1 Specific Metrics

L.SkewTop=Skew($\overline{y_1}$,average k=1:5,1)     47

R.SkewTop=Skew($\overline{y_2}$,average k=1:5,1)     48

L.SkewRit=Skew($\overline{x_1}$,average k=1:5,2)     49

R.SkewRit=Skew($\overline{x_2}$,average k=1:5,2)     50

L.SkewBot=Skew($\overline{y_1}$,average k=1:5,3)     51

R.SkewBot=Skew($\overline{y_2}$,average k=1:5,3)     52

L.SkewLef=Skew($\overline{x_1}$,average k=1:5,4)     53

R.SkewLef=Skew($\overline{x_2}$,average k=1:5,4)     54

2.6 Segment Normalized Skew $$SkewNorm(\overline{x_{j,k,l}}) = 3 * \frac{\text{Skew}(\overline{x_{j,k,l}})}{\sigma_{\overline{x_{j,k,l}}}}, \quad 55$$

$$SkewNorm(\overline{y_{j,k,l}}) = 3 * \frac{\text{Skew}(\overline{y_{j,k,l}})}{\sigma_{\overline{y_{j,k,l}}}}. \quad 56$$

2.6.1 Specific Metrics

L.SkewTopNorm=SkewNorm($\overline{y_1}$,average k=1:5,1)     57

R.SkewTopNorm=SkewNorm($\overline{y_2}$,average k=1:5,1)     58

L.SkewRitNorm=SkewNorm($\overline{x_1}$,average k=1:5,2)     59

R.SkewRitNorm=SkewNorm($\overline{x_2}$,average k=1:5,2)     60

L.SkewBotNorm=SkewNorm($\overline{y_1}$,average k=1:5,3)     61

R.SkewBotNorm=SkewNorm($\overline{y_2}$,average k=1:5,3)     62

L.SkewLefNorm=SkewNorm($\overline{x_1}$,average k=1:5,4)     63

R.SkewLefNorm=SkewNorm($\overline{x_2}$,average k=1:5,4)     64

2.7 BOX Height Mean

BoxHeightMean$_j$=$\overline{y}_{j,average\ k=1:5,1}$ − $\overline{y}_{j,average\ k=1:5,3}$     65

2.7.1 Left Height Mean

LeftBoxHeightMean=BoxHeightMean$_1$     66

2.7.2 Right Height Mean

RightBoxHeightMean=BoxHeightMean$_2$     67

2.8 Box Height Median

BoxHeightMedian$_j$=$\widetilde{y}_{j,average\ k=1:5,1}$ − $\widetilde{y}_{j,average\ k=1:5,3}$     68

2.8.1 Left Box Height Median

LeftBoxHeightMedian=BoxHeightMedian$_1$     69

2.8.2 Right Box Height Median

RightBoxHeightMedian=BoxHeightMedian$_2$     70

2.9 Box Width Mean

BoxWidthMean$_j$=$\overline{x}_{j,average\ k=1:5,2}$ − $\overline{x}_{j,average\ k=1:5,4}$     71

2.9.1 Left Box Width Mean

LeftBoxWidthMean=BoxWidthMean$_1$     72

2.9.2 Right Box Width Mean

RightBoxWidthMean=BoxWidthMean$_2$     73

2.10 Box Width Median

BoxWidthMedian$_j$=$\widetilde{x}_{j,average\ k=1:5,2}$ − $\widetilde{x}_{j,average\ k=1:5,4}$     74

2.10.1 Left box width median

LeftBoxWidthMedian=BoxWidthMedian$_1$     75

2.10.2 Right Box Width Median

RightBoxWidthMedian=BoxWidthMedian$_2$     76

2.11 Box Aspect Ratio Mean $$AspectRatioMean_j = \frac{BoxHeightMean_j}{BoxWidthMean_j} \quad 77$$

2.11.1 Left Box Aspect Ratio Mean $$LeftAspectRatioMean = \frac{LeftBoxHeightMean}{LeftBoxWidthMean} \qquad (78)$$

2.11.2 Right Box Aspect Ratio Mean $$RightAspectRatioMean = \frac{RightBoxHeightMean}{RightBoxWidthMean} \qquad (79)$$

2.12 Box Aspect Ratio Median $$AspectRatioMedian_j = \frac{BoxHeightMedian_j}{BoxWidthMedian_j} \qquad (80)$$

2.12.1 Left Box Aspect Ratio Median $$LeftAspectRatioMedian = \frac{LeftBoxHeightMedian}{leftBoxWidthMedian} \qquad (81)$$

2.12.2 Right Box Aspect Ratio Median $$RightAspectRatioMedian = \frac{RightBoxHeightMedian}{RightBoxWidthMedian} \qquad (82)$$

2.13 Box Area Mean $$BoxAreaMean_j = BoxHeightMean_j \times BoxWidthMean_j \qquad (83)$$

2.13.1 Left Box Area Mean $$LeftBoxAreaMean = LeftBoxHeightMean \times LeftBoxWidthMean \qquad (84)$$

2.13.2 Right Box Area Mean $$RightBoxAreaMean = RightBoxHeightMean \times RightBoxWidthMean \qquad (85)$$

2.14 Box Area Median $$BoxAreaMedian_j = BoxHeightMedian_j \times BoxWidthMedian_j \qquad (86)$$

2.14.1 Left Box Area Median $$LeftBoxAreaMedian = LeftBoxHeightMedian \times LeftBoxWidthMedian \qquad (87)$$

2.14.2 Right Box Area Median $$RightBoxAreaMedian = RigthBoxHeightMedian \times RightBoxWidthMedian \qquad (88)$$

2.15 Segment Distance

The segment distance is calculated by adding the distances travelled during each unit time for that segment.

$$SegDist_{j,k,l} = \frac{\sum D_{j,k,l}}{\Sigma(D_{j,k,l} \cap \mathbb{R})} \qquad (89)$$

The segment distance for the average cycle (cycle whose data points are obtained by averaging five cycles) can be represented as:

$$SegDist'_{j,l} = \frac{\sum D'_{j,l}}{\Sigma(D'_{j,l} \cap \mathbb{R})} \qquad (90)$$

2.15.1 Specific Metrics $$L.DistTop = \frac{\sum D'_{1,1}}{\Sigma(D'_{1,1} \cap \mathbb{R})} \qquad (91)$$

$$R.DistTop = \frac{\sum D'_{2,1}}{\Sigma(D'_{2,1} \cap \mathbb{R})} \qquad (92)$$

$$L.DistRit = \frac{\sum D'_{1,2}}{\Sigma(D'_{1,2} \cap \mathbb{R})} \qquad (93)$$

$$R.DistRit = \frac{\sum D'_{2,2}}{\Sigma(D'_{2,2} \cap \mathbb{R})} \qquad (94)$$

$$L.DistBot = \frac{\sum D'_{1,3}}{\Sigma(D'_{1,13} \cap \mathbb{R})} \qquad (95)$$

$$R.DistBot = \frac{\sum D'_{2,3}}{\Sigma(D'_{2,3} \cap \mathbb{R})} \qquad (96)$$

$$L.DistLef = \frac{\sum D'_{1,4}}{\Sigma(D'_{1,4} \cap \mathbb{R})} \qquad (97)$$

$$R.DistLef = \frac{\sum D'_{2,4}}{\Sigma(D'_{2,4} \cap \mathbb{R})} \qquad (98)$$

2.16 Conjugacy

The five cycles, and their average cycle is averaged together (notice six cycles being averaged) rendering:

$$\hat{x}_{j,l} \qquad (99)$$

$$\hat{y}_{j,l} \qquad (100)$$

Then the data from the right eye is subtracted from the left eye to obtain a delta value:

$$\hat{x}_l = \hat{x}_{1,j,l} - \hat{x}_{2,j,l} \qquad (101)$$

$$\hat{y}_l = \hat{y}_{1,j,l} - \hat{y}_{2,j,l} \qquad (102)$$

Here l corresponds to the top, right, bottom and left segments of the box.

The missing data in $x_i$ or $y_i$ is treated as NaN. The total number of non-missing coordinates can be calculated as follows:

$$NonMissingX(l) = \Sigma(\hat{x}_l \cap \mathbb{R}) \qquad (103)$$

$$NonMissingY(l) = \Sigma(\hat{y}_l \cap \mathbb{R}) \qquad (104)$$

Hence the NonMissingX or NonMissingY will represent the COUNT of all non-nan values instead of their sum.

2.17 Variance (Conjugacy)

The variance here does not follow the traditional form of statistical variance. In the traditional form, the average of the data points is subtracted from the sum of individual data points. In this case, the average is forced to zero, thus inferring that the hypothetical control patient has perfect conjugacy (left and right eye move precisely together).

$$Conj\ varX = Var(\hat{x}) = \frac{\sum_{l=1}^{4}(\hat{x}_l^2)}{NonMissingX(l=1:4)} \quad 105$$

$$Conj\ varY = Var(\hat{y}) = \frac{\sum_{l=1}^{4}(\hat{y}_l^2)}{NonMissingY(l=1:4)} \quad 106$$

$$TotalVariance = Conj\ totVar = Var(\hat{x}) + Var(\hat{y}) \quad 107$$

$$CoVariance = Conj\ CorrXY = \frac{\sum_{l=1}^{4}\hat{x}_l\hat{y}_l}{NonMissingX(l=1:4)-1} \quad 108$$

2.17.1 Specific Metrics $$Conj\ varXtop = \frac{\widehat{x_1}^2}{NonMissingX(l=1)} \quad 109$$

In the equation above, all the individual pupil x coordinate positions in the segment no. 1 $\hat{x}_1$ are added after squaring them before dividing them with NonMissingX(l=1). This is true for all equations below in this section as well.

$$Conj\ varXrit = \frac{\widehat{x_2}^2}{NonMissingX(l=2)} \quad 110$$

$$Conj\ varXbot = \frac{\widehat{x_3}^2}{NonMissingX(l=3)} \quad 111$$

$$Conj\ varXlef = \frac{\widehat{x_4}^2}{NonMissingX(l=4)} \quad 112$$

$$Conj\ varYtop = \frac{\widehat{y_1}^2}{NonMissingY(l=1)} \quad 113$$

$$Conj\ varYrit = \frac{\widehat{y_2}^2}{NonMissingY(l=2)} \quad 114$$

$$Conj\ varYbot = \frac{\widehat{y_3}^2}{NonMissingY(l=3)} \quad 115$$

$$Conj\ varYlef = \frac{\widehat{y_4}^2}{NonMissingY(l=4)} \quad 116$$

2.18 Variance x Ratio Top/Bottom (Conjugacy)

$$Conj\ VarXtopbotRatio = \frac{Conj\ varXtop}{Conj\ varXbot} \quad 117$$

2.19 Variance y Ratio Top/Bottom (Conjugacy)

$$Conj\ VarYtopbotRatio = \frac{Conj\ varYtop}{Conj\ varYbot} \quad 118$$

2.20 Variance x Ratio Left/Right (Conjugacy)

$$Conj\ VarXlefritRatio = \frac{Conj\ varXlef}{Conj\ varXrit} \quad 119$$

2.21 Variance y Ratio Left/Right (Conjugacy)

$$Conj\ VarYlefritRatio = \frac{Conj\ varXlef}{Conj\ varXrit} \quad 120$$

2.22 Difference in Aspect Ratio of Left/Right Eye $$Conj\ \Delta Aspect = AspectRatioMedian_{1,1:5} - AspectRatioMedian_{2,1:5} \quad 121$$

2.23 Variance of ΔAspect (Conjugacy)

$$Conj\ varY = Var(\hat{y}) = \frac{\sum_{k=1}^{5} Conj\ \Delta Aspect^2}{\Sigma(Conj\ \Delta Aspect \cap \mathbb{R})} \quad 122$$

2.24 Segment Velocity

The segment velocity is the average velocity in each unit time during that segment, and can be represented as:

$$AvgVel_{j,k,l} = Average(V_{j,k,l}) \quad 123$$

The segment velocity for the average cycle (cycle whose data points are obtained by averaging five cycles) can be represented as:

$$AvgVel'_{j,l} = Average(V'_{j,l}) \quad 124$$

2.24.1 Specific Metrics $$L.VelTop = Average(V'_{1,1}) \quad 125$$

$$R.VelTop = Average(V'_{2,1}) \quad 126$$

$$L.VelRit = Average(V'_{1,2}) \quad 127$$

$$R.VelRit = Average(V'_{2,2}) \quad 128$$

$$L.VelBot = Average(V'_{1,3}) \quad 129$$

$$R.VelBot = Average(V'_{2,3}) \quad 130$$

$$L.VelLef = Average(V'_{1,4}) \quad 131$$

$$R.VelLef = Average(V'_{2,4}) \quad 132$$

$$Conj.VelTop = L.VelTop - R.VelTop \quad 133$$

$$Conj.VelRit = L.VelRit - R.VelRit \quad 134$$

$$Conj.VelBot = L.VelBot - R.VelBot \quad 135$$

$$Conj.VelLef = L.VelLef - R.VelLef \quad 136$$

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

All references disclosed herein, whether patent or non-patent, are hereby incorporated by reference as if each was included at its citation, in its entirety. In case of conflict between reference and specification, the present specification, including definitions, will control.

Although the present disclosure has been described with a certain degree of particularity, it is understood the disclosure has been made by way of example, and changes in detail or structure may be made without departing from the spirit of the disclosure as defined in the appended claims.

We claim:

1. A method for identifying whether a patient has been exposed to a blast or a pressure wave or a sonic wave by:
   (a) providing a display for presenting a visual stimulus and a camera;
   (b) seating the patient a predetermined distance away from the display;
   (c) presenting a video on the display to the patient, wherein the presenting a video on the display comprises presenting a video in an aperture that continuously moves along an outer perimeter of the display;
   (d) tracking eye movement of both eyes of the patient using the camera as the subject watches the video on the display and responds to the visual stimulus;
   (e) analyzing eye movement of both eyes of the patient in response to the visual stimulus on the display;
   (f) identifying the patient as having eye movements that are significantly different from eye movements of normal eyes; and
   (g) calculating a blast impact score that reflects a likelihood that the patient suffers from a blast brain injury based on age, gender, and eye conjugacy.

2. A method according to claim 1 wherein at least about 100,000 samples of eye position are obtained.

3. A method according to claim 1 wherein eye movement is tracked for a period of from about 30 to about 500 seconds.

4. A method according to claim 1 wherein analyzing eye movement of both eyes comprises generating and plotting pairs of (x,y) values representing two components of instantaneous angle of pupil reflection (horizontal, vertical) over a period of time.

5. A method according to claim 1 wherein analyzing eye movement of both eyes comprises generating figures substantially resembling boxes that reflect a trajectory traveled by a visual stimulation.

6. A method according to claim 1 wherein identifying the patient as having eye movement of a first eye that is significantly different from eye movement of a second eye comprises identifying patients having a movement measure outlying the bell curve of normals.

7. A method according to claim 1, wherein a blast impact score of greater than or equal to 10.75 indicates the presence of a blast brain injury.

8. A method according to claim 1, further comprising correlating the blast impact score with the patient's distance from a blast epicenter.

9. A method according to claim 1, wherein the blast impact score is calculated to be equal to $\exp(y)/(1+\exp(y))*100$, where
   $y = -2.569133882 + 0.01245639*age - 0.517373229*gender + 16.57131011*conjvarXtop + 0.057694955*age*gender - 2060.801989*gender*conjvarXtop$, where gender is 1 if male, and 0 if female.

* * * * *